United States Patent [19]

McKerrow et al.

[11] Patent Number: 5,284,829
[45] Date of Patent: Feb. 8, 1994

[54] SYNTHETIC TETRAPEPTIDES FOR THE PREVENTION OF SCHISTOSOME PARASITE INFECTION

[75] Inventors: James H. McKerrow; Fred E. Cohen, both of San Francisco, Calif.

[73] Assignee: The Regents of the University of California, Oakland, Calif.

[21] Appl. No.: 798,565

[22] Filed: Nov. 26, 1991

[51] Int. Cl.$^5$ ...................... A61K 37/10; A61K 37/02
[52] U.S. Cl. ......................................... 514/18; 514/19; 514/846; 514/969; 530/323; 530/330; 530/331
[58] Field of Search ................... 514/18, 19, 846, 969; 530/323, 330, 331

[56] References Cited

U.S. PATENT DOCUMENTS

| | | | |
|---|---|---|---|
| 3,806,598 | 4/1974 | Alderman et al. | 514/446 |
| 4,518,528 | 5/1985 | Rasnick | 548/533 |
| 4,659,738 | 4/1987 | Miller et al. | 514/514 |

OTHER PUBLICATIONS

Powers, J. C. and Tuhy, P. M., *Biochemistry* 12, 4767-4774 (1973).
Cherfas, J., *Science* 246, 1242-1232 (1989).
McKerrow, J. H., Pino-Heiss, S., Lindquist, R. and Werb, Z. *Journal of Biological Chemistry*, 160, 3703-3707 (1985).
Newport, G. R., McKerrow, J. H., Hedstrom, R., Petitt, M. McGarrigle, L. Barr, P. J. and Agabian, N., *Journal of Biological Chemistry* 263, 13179-13184 (1988).
McKerrow, J. H., Skanari, J., Brown, M., Brindley, P., Railey, J., Weiss, N., and Resnick, S. D., *Models in Dermatology*, vol. 4, 276-284 (1989).
Amiri, F., Cohen, F. E., Gregoret, L. M., Aldape, K., Railey, J., and McKerrow, J. H., Abstrcts of the 20th Annual Meetings for the Keystone Symposia on Molecular and Cellular Biology (1991).

*Primary Examiner*—Ronald W. Griffin
*Attorney, Agent, or Firm*—Robbins, Berliner & Carson

[57] ABSTRACT

The invention relates to synthetic tetrapeptides that contain a peptide blocking group at the amino terminus and an enzyme inhibitor at the carboxy terminus, and their use in the prevention of schistosome parasite infection.

16 Claims, 3 Drawing Sheets

SEQUENCE LISTING ( 1 ) GENERAL INFORMATION:

( i i i ) NUMBER OF SEQUENCES: 147

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:
        Ala  Ala  Pro  Trp
        1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:
        Ala  Gly  Pro  Ala
        1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:
        Ala Gly Pro Leu
        1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:
        Ala Gly Pro Xaa
        1

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:
        Ala Gly Pro Met
        1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:
        Ala Gly Pro Phe
        1

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:
        Ala Gly Pro Trp
        1

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:
        Ala Gly Pro Val
        1

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:
        Ala Lys Pro Ala
        1

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:
        Ala Lys Pro Leu
        1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:
        Ala Lys Pro Xaa
        1

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:
        Ala Lys Pro Met
        1

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:
        Ala Lys Pro Phe
        1

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:
        Ala Lys Pro Trp
        1

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:
        Ala Lys Pro Val
        1

( 2 ) INFORMATION FOR SEQ ID NO:16:

( i ) SEQUENCE CHARACTERISTICS:

(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:16:
    Gly Ala Pro Ala
    1

(2) INFORMATION FOR SEQ ID NO:17:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (xi) SEQUENCE DESCRIPTION: SEQ ID NO:17:
    Gly Ala Pro Leu
    1

(2) INFORMATION FOR SEQ ID NO:18:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (xi) SEQUENCE DESCRIPTION: SEQ ID NO:18:
    Gly Ala Pro Xaa
    1

(2) INFORMATION FOR SEQ ID NO:19:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (xi) SEQUENCE DESCRIPTION: SEQ ID NO:19:
    Gly Ala Pro Met
    1

(2) INFORMATION FOR SEQ ID NO:20:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (xi) SEQUENCE DESCRIPTION: SEQ ID NO:20:
    Gly Ala Pro Phe
    1

(2) INFORMATION FOR SEQ ID NO:21:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (xi) SEQUENCE DESCRIPTION: SEQ ID NO:21:
    Gly Ala Pro Trp
    1

(2) INFORMATION FOR SEQ ID NO:22:

(i) SEQUENCE CHARACTERISTICS:
    (A) LENGTH: 4 amino acids
    (B) TYPE: amino acid
    (D) TOPOLOGY: linear ( i i ) MOLECULE TYPE: peptide ( x i ) SEQUENCE DESCRIPTION: SEQ ID NO:22:
        Gly Ala Pro Val
        1

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:
        Gly Gly Pro Ala
        1

( 2 ) INFORMATION FOR SEQ ID NO:24:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:
        Gly Gly Pro Leu
        1

( 2 ) INFORMATION FOR SEQ ID NO:25:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:
        Gly Gly Pro Xaa
        1

( 2 ) INFORMATION FOR SEQ ID NO:26:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:
        Gly Gly Pro Met
        1

( 2 ) INFORMATION FOR SEQ ID NO:27:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:
        Gly Gly Pro Phe
        1

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:
        Gly Gly Pro Trp ( 2 ) INFORMATION FOR SEQ ID NO:29:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:
        Gly Gly Pro Val
        1

( 2 ) INFORMATION FOR SEQ ID NO:30:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:
        Gly Lys Pro Ala
        1

( 2 ) INFORMATION FOR SEQ ID NO:31:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:
        Gly Lys Pro Leu
        1

( 2 ) INFORMATION FOR SEQ ID NO:32:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:
        Gly Lys Pro Xaa
        1

( 2 ) INFORMATION FOR SEQ ID NO:33:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:
        Gly Lys Pro Met
        1

( 2 ) INFORMATION FOR SEQ ID NO:34:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:
        Gly Lys Pro Phe
        1

( 2 ) INFORMATION FOR SEQ ID NO:35:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:35:
    Gly Lys Pro Trp
    1

( 2 ) INFORMATION FOR SEQ ID NO:36:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:36:
    Gly Lys Pro Val
    1

( 2 ) INFORMATION FOR SEQ ID NO:37:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:37:
    Trp Ala Pro Ala
    1

( 2 ) INFORMATION FOR SEQ ID NO:38:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:38:
    Trp Ala Pro Leu
    1

( 2 ) INFORMATION FOR SEQ ID NO:39:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:39:
    Trp Ala Pro Xaa
    1

( 2 ) INFORMATION FOR SEQ ID NO:40:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:40:
    Trp Ala Pro Met
    1

( 2 ) INFORMATION FOR SEQ ID NO:41:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:41:
      Trp Ala Pro Phe
      1

( 2 ) INFORMATION FOR SEQ ID NO:42:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:
      Trp Ala Pro Trp
      1

( 2 ) INFORMATION FOR SEQ ID NO:43:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:
      Trp Ala Pro Val
      1

( 2 ) INFORMATION FOR SEQ ID NO:44:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:
      Trp Gly Pro Ala
      1

( 2 ) INFORMATION FOR SEQ ID NO:45:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:
      Trp Gly Pro Leu
      1

( 2 ) INFORMATION FOR SEQ ID NO:46:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:
      Trp Gly Pro Xaa
      1

( 2 ) INFORMATION FOR SEQ ID NO:47:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

Trp Gly Pro Met
                1

( 2 ) INFORMATION FOR SEQ ID NO:48:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:
                Trp Gly Pro Phe
                1

( 2 ) INFORMATION FOR SEQ ID NO:49:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:
                Trp Gly Pro Trp
                1

( 2 ) INFORMATION FOR SEQ ID NO:50:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:50:
                Trp Gly Pro Val
                1

( 2 ) INFORMATION FOR SEQ ID NO:51:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:51:
                Trp Lys Pro Ala
                1

( 2 ) INFORMATION FOR SEQ ID NO:52:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:52:
                Trp Lys Pro Leu
                1

( 2 ) INFORMATION FOR SEQ ID NO:53:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:53:
                Trp Lys Pro Xaa
                1

( 2 ) INFORMATION FOR SEQ ID NO:54:

( i ) SEQUENCE CHARACTERISTICS:
     ( A ) LENGTH: 4 amino acids
     ( B ) TYPE: amino acid
     ( D ) TOPOLOGY: linear ( i i ) MOLECULE TYPE: peptide ( x i ) SEQUENCE DESCRIPTION: SEQ ID NO:54:
     Trp Lys Pro Met
     1

( 2 ) INFORMATION FOR SEQ ID NO:55:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:55:
          Trp Lys Pro Phe
          1

( 2 ) INFORMATION FOR SEQ ID NO:56:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:56:
          Trp Lys Pro Trp
          1

( 2 ) INFORMATION FOR SEQ ID NO:57:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:57:
          Trp Lys Pro Val
          1

( 2 ) INFORMATION FOR SEQ ID NO:58:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:58:
          Phe Ala Pro Ala
          1

( 2 ) INFORMATION FOR SEQ ID NO:59:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:59:
          Phe Ala Pro Leu
          1

( 2 ) INFORMATION FOR SEQ ID NO:60:

( i ) SEQUENCE CHARACTERISTICS:
          ( A ) LENGTH: 4 amino acids
          ( B ) TYPE: amino acid ( D ) TOPOLOGY: linear ( i i ) MOLECULE TYPE: peptide ( x i ) SEQUENCE DESCRIPTION: SEQ ID NO:60:
        Phe Ala Pro Xaa
        1

( 2 ) INFORMATION FOR SEQ ID NO:61:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:61:
        Phe Ala Pro Met
        1

( 2 ) INFORMATION FOR SEQ ID NO:62:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:62:
        Phe Ala Pro Phe
        1

( 2 ) INFORMATION FOR SEQ ID NO:63:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:63:
        Phe Ala Pro Trp
        1

( 2 ) INFORMATION FOR SEQ ID NO:64:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:64:
        Phe Ala Pro Val
        1

( 2 ) INFORMATION FOR SEQ ID NO:65:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:65:
        Phe Gly Pro Ala
        1

( 2 ) INFORMATION FOR SEQ ID NO:66:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:66:
Phe Gly Pro Leu
1

( 2 ) INFORMATION FOR SEQ ID NO:67:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:67:
Phe Gly Pro Xaa
1

( 2 ) INFORMATION FOR SEQ ID NO:68:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:68:
Phe Gly Pro Met
1

( 2 ) INFORMATION FOR SEQ ID NO:69:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:69:
Phe Gly Pro Phe
1

( 2 ) INFORMATION FOR SEQ ID NO:70:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:70:
Phe Gly Pro Trp
1

( 2 ) INFORMATION FOR SEQ ID NO:71:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:71:
Phe Gly Pro Val
1

( 2 ) INFORMATION FOR SEQ ID NO:72:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:72:
Phe Lys Pro Ala
1

(2) INFORMATION FOR SEQ ID NO:73:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:73:
Phe Lys Pro Leu
1

(2) INFORMATION FOR SEQ ID NO:74:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:74:
Phe Lys Pro Xaa
1

(2) INFORMATION FOR SEQ ID NO:75:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:75:
Phe Lys Pro Met
1

(2) INFORMATION FOR SEQ ID NO:76:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:76:
Phe Lys Pro Phe
1

(2) INFORMATION FOR SEQ ID NO:77:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:77:
Phe Lys Pro Trp
1

(2) INFORMATION FOR SEQ ID NO:78:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:78:
Phe Lys Pro Val
1

(2) INFORMATION FOR SEQ ID NO:79:

(i) SEQUENCE CHARACTERISTICS:
(A) LENGTH: 4 amino acids (B) TYPE: amino acid
(D) TOPOLOGY: linear (ii) MOLECULE TYPE: peptide (xi) SEQUENCE DESCRIPTION: SEQ ID NO:79:
Xaa Ala Pro Ala
1

(2) INFORMATION FOR SEQ ID NO:80:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:80:
Xaa Ala Pro Leu
1

(2) INFORMATION FOR SEQ ID NO:81:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:81:
Xaa Ala Pro Xaa
1

(2) INFORMATION FOR SEQ ID NO:82:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:82:
Xaa Ala Pro Met
1

(2) INFORMATION FOR SEQ ID NO:83:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:83:
Xaa Ala Pro Phe
1

(2) INFORMATION FOR SEQ ID NO:84:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:84:
Xaa Ala Pro Trp
1

(2) INFORMATION FOR SEQ ID NO:85:

(i) SEQUENCE CHARACTERISTICS:
(A) LENGTH: 4 amino acids
(B) TYPE: amino acid
(D) TOPOLOGY: linear (ii) MOLECULE TYPE: peptide (x i) SEQUENCE DESCRIPTION: SEQ ID NO:85:
　　　　　　　　Xaa Ala Pro Val
　　　　　　　　1

(2) INFORMATION FOR SEQ ID NO:86:

(i) SEQUENCE CHARACTERISTICS:
　　　　(A) LENGTH: 4 amino acids
　　　　(B) TYPE: amino acid
　　　　(D) TOPOLOGY: linear (i i) MOLECULE TYPE: peptide (x i) SEQUENCE DESCRIPTION: SEQ ID NO:86:
　　　　　　　　Xaa Gly Pro Ala
　　　　　　　　1

(2) INFORMATION FOR SEQ ID NO:87:

(i) SEQUENCE CHARACTERISTICS:
　　　　(A) LENGTH: 4 amino acids
　　　　(B) TYPE: amino acid
　　　　(D) TOPOLOGY: linear (i i) MOLECULE TYPE: peptide (x i) SEQUENCE DESCRIPTION: SEQ ID NO:87:
　　　　　　　　Xaa Gly Pro Leu
　　　　　　　　1

(2) INFORMATION FOR SEQ ID NO:88:

(i) SEQUENCE CHARACTERISTICS:
　　　　(A) LENGTH: 4 amino acids
　　　　(B) TYPE: amino acid
　　　　(D) TOPOLOGY: linear (i i) MOLECULE TYPE: peptide (x i) SEQUENCE DESCRIPTION: SEQ ID NO:88:
　　　　　　　　Xaa Gly Pro Xaa
　　　　　　　　1

(2) INFORMATION FOR SEQ ID NO:89:

(i) SEQUENCE CHARACTERISTICS:
　　　　(A) LENGTH: 4 amino acids
　　　　(B) TYPE: amino acid
　　　　(D) TOPOLOGY: linear (i i) MOLECULE TYPE: peptide (x i) SEQUENCE DESCRIPTION: SEQ ID NO:89:
　　　　　　　　Xaa Gly Pro Met
　　　　　　　　1

(2) INFORMATION FOR SEQ ID NO:90:

(i) SEQUENCE CHARACTERISTICS:
　　　　(A) LENGTH: 4 amino acids
　　　　(B) TYPE: amino acid
　　　　(D) TOPOLOGY: linear (i i) MOLECULE TYPE: peptide (x i) SEQUENCE DESCRIPTION: SEQ ID NO:90:
　　　　　　　　Xaa Gly Pro Phe
　　　　　　　　1

(2) INFORMATION FOR SEQ ID NO:91:

(i) SEQUENCE CHARACTERISTICS:
　　　　(A) LENGTH: 4 amino acids
　　　　(B) TYPE: amino acid
　　　　(D) TOPOLOGY: linear (i i) MOLECULE TYPE: peptide (x i) SEQUENCE DESCRIPTION: SEQ ID NO:91:
　　　　　　　　Xaa Gly Pro Trp
　　　　　　　　1

( 2 ) INFORMATION FOR SEQ ID NO:92:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:92:
        Xaa Gly Pro Val
        1

( 2 ) INFORMATION FOR SEQ ID NO:93:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:93:
        Xaa Lys Pro Ala
        1

( 2 ) INFORMATION FOR SEQ ID NO:94:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:94:
        Xaa Lys Pro Leu
        1

( 2 ) INFORMATION FOR SEQ ID NO:95:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:95:
        Xaa Lys Pro Xaa
        1

( 2 ) INFORMATION FOR SEQ ID NO:96:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:96:
        Xaa Lys Pro Met
        1

( 2 ) INFORMATION FOR SEQ ID NO:97:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:97:
        Xaa Lys Pro Phe
        1

( 2 ) INFORMATION FOR SEQ ID NO:98:

( i ) SEQUENCE CHARACTERISTICS:

( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:98:

Xaa Lys Pro Trp
1

( 2 ) INFORMATION FOR SEQ ID NO:99:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:99:

Xaa Lys Pro Val
1

( 2 ) INFORMATION FOR SEQ ID NO:100:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:100:

Xaa Ala Pro Ala
1

( 2 ) INFORMATION FOR SEQ ID NO:101:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:101:

Xaa Ala Pro Leu
1

( 2 ) INFORMATION FOR SEQ ID NO:102:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:102:

Xaa Ala Pro Xaa
1

( 2 ) INFORMATION FOR SEQ ID NO:103:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:103:

Xaa Ala Pro Met
1

( 2 ) INFORMATION FOR SEQ ID NO:104:

( i ) SEQUENCE CHARACTERISTICS:
( A ) LENGTH: 4 amino acids
( B ) TYPE: amino acid
( D ) TOPOLOGY: linear (i i) MOLECULE TYPE: peptide (x i) SEQUENCE DESCRIPTION: SEQ ID NO:104:

Xaa Ala Pro Phe
1

(2) INFORMATION FOR SEQ ID NO:105:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:105:

Xaa Ala Pro Trp
1

(2) INFORMATION FOR SEQ ID NO:106:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:106:

Xaa Ala Pro Val
1

(2) INFORMATION FOR SEQ ID NO:107:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:107:

Xaa Ala Pro Ala
1

(2) INFORMATION FOR SEQ ID NO:108:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:108:

Xaa Ala Pro Leu
1

(2) INFORMATION FOR SEQ ID NO:109:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:109:

Xaa Gly Pro Xaa
1

(2) INFORMATION FOR SEQ ID NO:110:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:110:

Xaa Gly Pro Met ( 2 ) INFORMATION FOR SEQ ID NO:111:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:111:
        Xaa Gly Pro Phe
        1

( 2 ) INFORMATION FOR SEQ ID NO:112:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:112:
        Xaa Gly Pro Trp
        1

( 2 ) INFORMATION FOR SEQ ID NO:113:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:113:
        Xaa Gly Pro Val
        1

( 2 ) INFORMATION FOR SEQ ID NO:114:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:114:
        Xaa Lys Pro Ala
        1

( 2 ) INFORMATION FOR SEQ ID NO:115:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:115:
        Xaa Lys Pro Leu
        1

( 2 ) INFORMATION FOR SEQ ID NO:116:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:116:
        Xaa Lys Pro Xaa
        1

( 2 ) INFORMATION FOR SEQ ID NO:117:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:117:

Xaa Lys Pro Met
1

( 2 ) INFORMATION FOR SEQ ID NO:118:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:118:

Xaa Lys Pro Phe
1

( 2 ) INFORMATION FOR SEQ ID NO:119:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:119:

Xaa Lys Pro Trp
1

( 2 ) INFORMATION FOR SEQ ID NO:120:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:120:

Xaa Lys Pro Val
1

( 2 ) INFORMATION FOR SEQ ID NO:121:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:121:

Xaa Ala Pro Ala
1

( 2 ) INFORMATION FOR SEQ ID NO:122:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:122:

Xaa Ala Pro Leu
1

( 2 ) INFORMATION FOR SEQ ID NO:123:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:123:
Xaa Lys Pro Xaa
1

( 2 ) INFORMATION FOR SEQ ID NO:124:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:124:
Xaa Ala Pro Met
1

( 2 ) INFORMATION FOR SEQ ID NO:125:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:125:
Xaa Ala Pro Phe
1

( 2 ) INFORMATION FOR SEQ ID NO:126:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:126:
Xaa Ala Pro Trp
1

( 2 ) INFORMATION FOR SEQ ID NO:127:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:127:
Xaa Ala Pro Val
1

( 2 ) INFORMATION FOR SEQ ID NO:128:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:128:
Xaa Gly Pro Ala
1

( 2 ) INFORMATION FOR SEQ ID NO:129:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:129:

```
              Xaa  Gly  Pro  Leu
              1
```

( 2 ) INFORMATION FOR SEQ ID NO:130:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:130:
```
              Xaa  Gly  Pro  Xaa
              1
```

( 2 ) INFORMATION FOR SEQ ID NO:131:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:131:
```
              Xaa  Gly  Pro  Met
              1
```

( 2 ) INFORMATION FOR SEQ ID NO:132:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:132:
```
              Xaa  Gly  Pro  Phe
              1
```

( 2 ) INFORMATION FOR SEQ ID NO:133:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:133:
```
              Xaa  Gly  Pro  Trp
              1
```

( 2 ) INFORMATION FOR SEQ ID NO:134:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:134:
```
              Xaa  Gly  Pro  Val
              1
```

( 2 ) INFORMATION FOR SEQ ID NO:135:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:135:
```
              Xaa  Lys  Pro  Ala
              1
```

( 2 ) INFORMATION FOR SEQ ID NO:136:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:136:
    Xaa Lys Pro Leu
    1

( 2 ) INFORMATION FOR SEQ ID NO:137:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:137:
        Xaa Lys Pro Xaa
        1

( 2 ) INFORMATION FOR SEQ ID NO:138:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:138:
        Xaa Lys Pro Met
        1

( 2 ) INFORMATION FOR SEQ ID NO:139:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:139:
        Xaa Lys Pro Phe
        1

( 2 ) INFORMATION FOR SEQ ID NO:140:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:140:
        Xaa Lys Pro Trp
        1

( 2 ) INFORMATION FOR SEQ ID NO:141:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:141:
        Xaa Lys Pro Val
        1

( 2 ) INFORMATION FOR SEQ ID NO:142:

( i ) SEQUENCE CHARACTERISTICS:
        ( A ) LENGTH: 4 amino acids
        ( B ) TYPE: amino acid (D) TOPOLOGY: linear (ii) MOLECULE TYPE: peptide (xi) SEQUENCE DESCRIPTION: SEQ ID NO:142:
            Ala Ala Pro Ala
            1

(2) INFORMATION FOR SEQ ID NO:143:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:143:
            Ala Ala Pro Leu
            1

(2) INFORMATION FOR SEQ ID NO:144:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:144:
            Ala Ala Pro Xaa
            1

(2) INFORMATION FOR SEQ ID NO:145:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:145:
            Ala Ala Pro Met
            1

(2) INFORMATION FOR SEQ ID NO:146:

(i) SEQUENCE CHARACTERISTICS:
        (A) LENGTH: 4 amino acids
        (B) TYPE: amino acid
        (D) TOPOLOGY: linear.

(ii) MOLECULE TYPE: peptide (xi) SEQUENCE DESCRIPTION: SEQ ID NO:146:
            Ala Ala Pro Phe
            1

(2) INFORMATION FOR SEQ ID NO:147:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:147:
            Ala Ala Pro Val
            1

SYNTHETIC TETRAPEPTIDES FOR THE PREVENTION OF SCHISTOSOME PARASITE INFECTION

ACKNOWLEDGMENT

This invention was made with Government support under Grant No. AI-20452, awarded by the National Institutes of Health, Contract No. MDA 972-91-J-1013, awarded by the Department of the Army and support from the Veterans Administration. The Government has certain rights in this invention.

FIELD OF THE INVENTION

This invention relates to synthetic enzyme inhibitors and their use in preventing parasite infection. More specifically, the invention relates to synthetic tetrapeptides that contain a peptide blocking group at the amino terminus and an enzyme inhibitor at the carboxy terminus, and their use in the prevention of schistosome parasite infection.

BACKGROUND

Schistosomiasis (bilharziasis) is a parasitic disease caused by schistosomes (blood flukes) that generally live in the veins of the gut and liver of a human host. Adult worms can survive up to 20 years, and heavy infestations block blood vessels. The mere presence of even a few adults acts as a focus of inflammation and infection. Worse, female adult worms release thousands of eggs each day, which often find their way to tissues such as liver, brain, and lung, where they cause considerable damage by stimulating the body to form cysts and scar tissue around them.

Most eggs, however, pass through the bladder or wall of the gut. Once outside, they hatch and infect water snails. The parasite multiplies inside the snail, giving rise to thousands of cercariae that exit the snail and swim free in search of a host in which to complete their life cycle. When the cercaria makes contact with skin, it releases a serine protease that dissolves the protein of the skin, affording entry into the body.

The World Health Organization estimates that over 200 million people worldwide suffer from schistosomiasis. Treatments are available, but because the disease is so debilitating, preventing the disease is preferable to treating it. This is especially true in the case of soldiers and engineers deployed in the tropics who must sometimes work in and around infested waters.

The United States Army has identified a compound that prevents infection by the schistosomiasis parasite. This compound, niclosamide, which was originally developed to kill snails, can be added to lotions, creams and sprays for topical administration, or can be incorporated into soap. See generally, Cherfas, J. 1989. *Science* 246, 1242–1243.

Despite the availability of niclosamide, there is a need for other anti-penetrant compounds that can inhibit invasion of skin by schistosome larvae. Accordingly, it is an object of the present invention to provide anti-penetrant compounds that can inhibit invasion of skin by schistosome larvae. Another object of the invention is to provide synthetic compounds that inhibit the enzyme(s) used by the schistosome larvae to invade skin. It is a further object of the present invention to provide compositions that contain synthetic compounds that inhibit serine protease(s). Such compositions can be applied topically via lotions, creams, sprays or soaps, etc., to inhibit or prevent cercariae from penetrating the skin.

SUMMARY OF THE INVENTION

To achieve the foregoing objects, the invention provides synthetic anti-penetrant compounds that are useful for inhibiting or preventing cercariae, the microscopic swimming stage of Schistosoma, from penetrating the skin. The compounds of the invention are broadly defined by the formula:

wherein: BG is a peptide blocking group; $AA_A$ is Ala, Gly, Trp, Phe, Adanantyl, Phenylglycine, or Hexafluoroisopropyl; $AA_B$ is Ala, Gly or Lys; $AA_C$ is Pro; $AA_D$ is Leu, Nle, Met, Phe, Trp, Val or Ala; and PI is a protease inhibitor.

The compounds of the invention can be incorporated into lotions, creams, sprays, soaps, etc., for use as anti-penetrants to inhibit or prevent cercariae from penetrating the skin.

DRAWINGS

FIG. 1. FIGS. 1(a and b) shows photomicrographs. FIG. 1a shows cercaria invading epidermis and dermis. Cross section of human skin X 250 original magnification. Hematoxylin and eosin stain. FIG. 1b shows cercariae bound to surface of skin but not invading in presence of 50 micromolar MeO-Suc-AAPL-CMK inhibitor. Assays were as described in Example IV.

FIG. 2 is a graph showing a comparison of effectiveness of peptide inhibitors in preventing skin invasion by cercariae at 50 micromolar. In the Figure: A-A-A-P-A-CMK=Ala-Ala-Ala-Pro-Ala-CMK; A-A-P-(D)boro-F-OH=Ala-Ala-Pro-(D)boro-Phe-OH; F-G-A-L-CMK=Phe-Gly-Ala-Leu-CMK; A-A-P-(L)boro-F-OH=Ala-Ala-Pro-(L)boro-Phe-OH; A-K-P-F-CMK=Ala-Lys-Pro-Phe-CMK; A-A-P-F-CMK=Ala-Ala-Pro-Phe-CMK; F-A-P-F-CMK=Phe-Ala-Pro-Phe-CMK; A-A-P-L-CMK=Ala-Ala-Pro-Leu-CMK. CMK=chloromethyl ketone.

FIG. 3 is a graph showing inhibition of cercariae invading skin by MeO-Suc-A-A-L(L)-boro-F-OH=MeO-Suc-Ala-Ala-Pro(L)-boro-Phe-OH.

DESCRIPTION OF THE SPECIFIC EMBODIMENTS

Figure 1A:
Figure 1B:
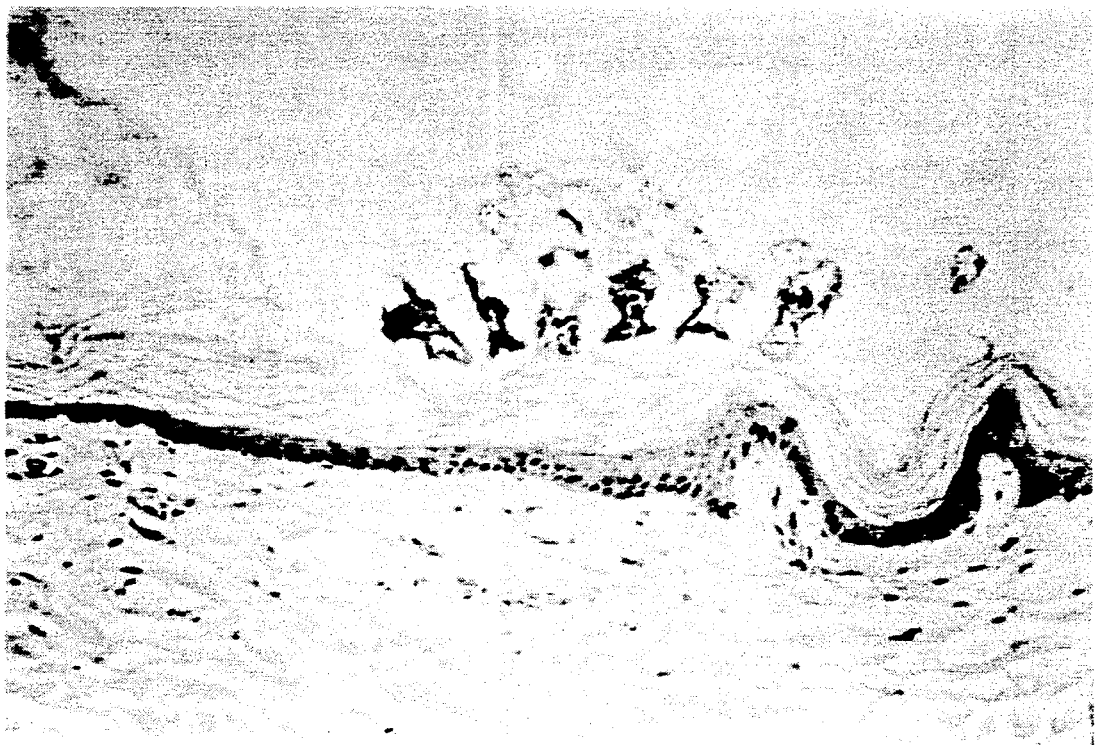
Figure 2:
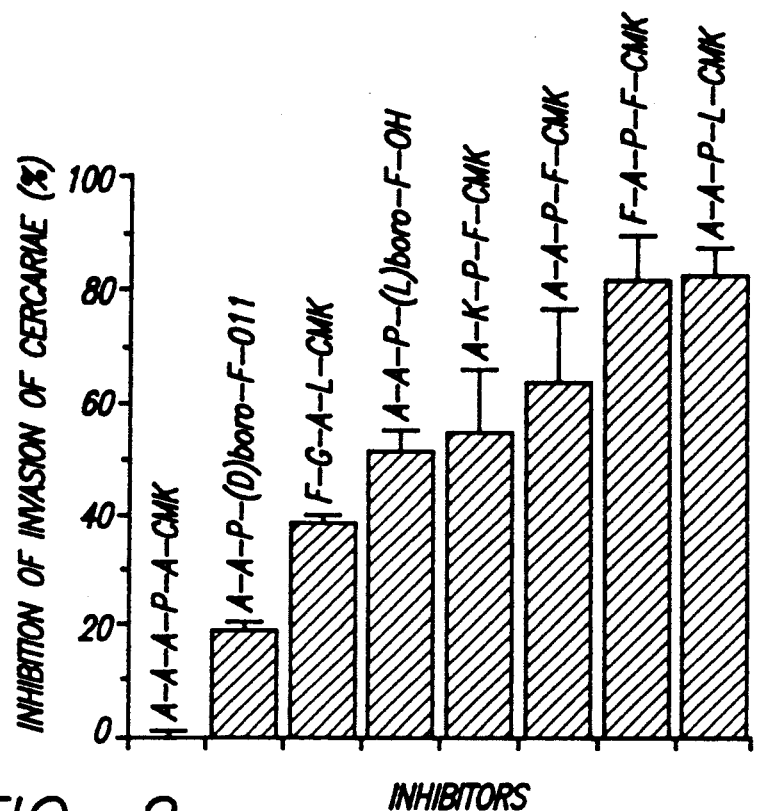
Figure 3:
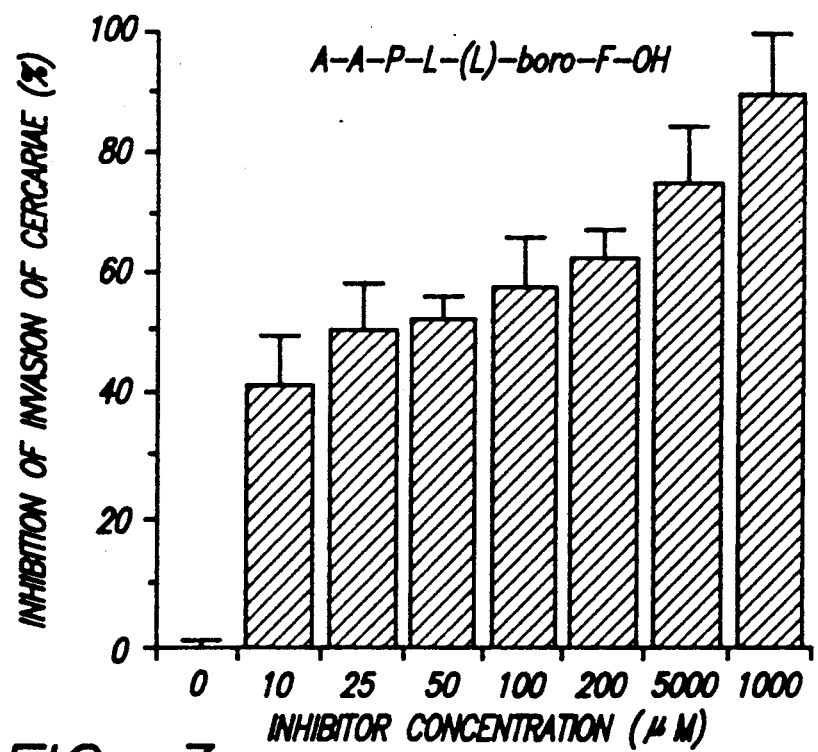

Using a three-dimensional computer model of parasite serine protease based upon the primary sequence of the enzyme and its homology with other serine proteases, tetrapeptide serine protease inhibitors were designed and constructed. The present invention provides these novel serine protease inhibitors which are broadly defined by the formula:

wherein: BG is a peptide blocking group; $AA_A$ is Ala, Gly, Trp, Phe, Adanantyl (referred to herein as Ada, and shown in the sequence listings as an Xaa), Phenylglycine (referred to herein as Pgl, and shown in the sequence listings as an Xaa), or Hexafluoroisopropyl (referred to herein as Hex, and shown in the sequence listings as an Xaa); $AA_B$ is Ala, Gly or Lys; $AA_C$ is Pro; $AA_D$ is Leu, Nle (Norleucine, which is shown in the sequence listings as an Xaa), Met, Phe, Trp, Val or Ala;

and PI is a protease inhibitor. Inhibitors of the invention include:

| | |
|---|---|
| BG-Ala-Ala-Pro-Trp-PI | (Ala-Ala-Pro-Trp = SEQ ID NO. 1) |
| BG-Ala-Gly-Pro-Ala-PI | (Ala-Gly-Pro-Ala = SEQ ID NO. 2) |
| BG-Ala-Gly-Pro-Leu-PI | (Ala-Gly-Pro-Leu = SEQ ID NO. 3) |
| BG-Ala-Gly-Pro-Nle-PI | (Ala-Gly-Pro-Xaa = SEQ ID NO. 4) |
| BG-Ala-Gly-Pro-Met-PI | (Ala-Gly-Pro-Met = SEQ ID NO. 5) |
| BG-Ala-Gly-Pro-Phe-PI | (Ala-Gly-Pro-Phe = SEQ ID NO. 6) |
| BG-Ala-Gly-Pro-Trp-PI | (Ala-Gly-Pro-Trp = SEQ ID NO. 7) |
| BG-Ala-Gly-Pro-Val-PI | (Ala-Gly-Pro-Val = SEQ ID NO. 8) |
| BG-Ala-Lys-Pro-Ala-PI | (Ala-Lys-Pro-Ala = SEQ ID NO. 9) |
| BG-Ala-Lys-Pro-Leu-PI | (Ala-Lys-Pro-Leu = SEQ ID NO. 10) |
| BG-Ala-Lys-Pro-Nle-PI | (Ala-Lys-Pro-Xaa = SEQ ID NO. 11) |
| BG-Ala-Lys-Pro-Met-PI | (Ala-Lys-Pro-Met = SEQ ID NO. 12) |
| BG-Ala-Lys-Pro-Phe-PI | (Ala-Lys-Pro-Phe = SEQ ID NO. 13) |
| BG-Ala-Lys-Pro-Trp-PI | (Ala-Lys-Pro-Trp = SEQ ID NO. 14) |
| BG-Ala-Lys-Pro-Val-PI | (Ala-Lys-Pro-Val = SEQ ID NO. 15) |
| BG-Gly-Ala-Pro-Ala-PI | (Gly-Ala-Pro-Ala = SEQ ID NO. 16) |
| BG-Gly-Ala-Pro-Leu-PI | (Gly-Ala-Pro-Leu = SEQ ID NO. 17) |
| BG-Gly-Ala-Pro-Nle-PI | (Gly-Ala-Pro-Xaa = SEQ ID NO. 18) |
| BG-Gly-Ala-Pro-Met-PI | (Gly-Ala-Pro-Met = SEQ ID NO. 19) |
| BG-Gly-Ala-Pro-Phe-PI | (Gly-Ala-Pro-Phe = SEQ ID NO. 20) |
| BG-Gly-Ala-Pro-Trp-PI | (Gly-Ala-Pro-Trp = SEQ ID NO. 21) |
| BG-Gly-Ala-Pro-Val-PI | (Gly-Ala-Pro-Val = SEQ ID NO. 22) |
| BG-Gly-Gly-Pro-Ala-PI | (Gly-Gly-Pro-Ala = SEQ ID NO. 23) |
| BG-Gly-Gly-Pro-Leu-PI | (Gly-Gly-Pro-Leu = SEQ ID NO. 24) |
| BG-Gly-Gly-Pro-Nle-PI | (Gly-Gly-Pro-Xaa = SEQ ID NO. 25) |
| BG-Gly-Gly-Pro-Met-PI | (Gly-Gly-Pro-Met = SEQ ID NO. 26) |
| BG-Gly-Gly-Pro-Phe-PI | (Gly-Gly-Pro-Phe = SEQ ID NO. 27) |
| BG-Gly-Gly-Pro-Trp-PI | (Gly-Gly-Pro-Trp = SEQ ID NO. 28) |
| BG-Gly-Gly-Pro-Val-PI | (Gly-Gly-Pro-Val = SEQ ID NO. 29) |
| BG-Gly-Lys-Pro-Ala-PI | (Gly-Lys-Pro-Ala = SEQ ID NO. 30) |
| BG-Gly-Lys-Pro-Leu-PI | (Gly-Lys-Pro-Leu = SEQ ID NO. 31) |
| BG-Gly-Lys-Pro-Nle-PI | (Gly-Lys-Pro-Xaa = SEQ ID NO. 32) |
| BG-Gly-Lys-Pro-Met-PI | (Gly-Lys-Pro-Met = SEQ ID NO. 33) |
| BG-Gly-Lys-Pro-Phe-PI | (Gly-Lys-Pro-Phe = SEQ ID NO. 34) |
| BG-Gly-Lys-Pro-Trp-PI | (Gly-Lys-Pro-Trp = SEQ ID NO. 35) |
| BG-Gly-Lys-Pro-Val-PI | (Gly-Lys-Pro-Val = SEQ ID NO. 36) |
| BG-Trp-Ala-Pro-Ala-PI | (Trp-Ala-Pro-Ala = SEQ ID NO. 37) |
| BG-Trp-Ala-Pro-Leu-PI | (Trp-Ala-Pro-Leu = SEQ ID NO. 38) |
| BG-Trp-Ala-Pro-Nle-PI | (Trp-Ala-Pro-Xaa = SEQ ID NO. 39) |
| BG-Trp-Ala-Pro-Met-PI | (Trp-Ala-Pro-Met = SEQ ID NO. 40) |
| BG-Trp-Ala-Pro-Phe-PI | (Trp-Ala-Pro-Phe = SEQ ID NO. 41) |
| BG-Trp-Ala-Pro-Trp-PI | (Trp-Ala-Pro-Trp = SEQ ID NO. 42) |
| BG-Trp-Ala-Pro-Val-PI | (Trp-Ala-Pro-Val = SEQ ID NO. 43) |
| BG-Trp-Gly-Pro-Ala-PI | (Trp-Gly-Pro-Ala = SEQ ID NO. 44) |
| BG-Trp-Gly-Pro-Leu-PI | (Trp-Gly-Pro-Leu = SEQ ID NO. 45) |
| BG-Trp-Gly-Pro-Nle-PI | (Trp-Gly-Pro-Xaa = SEQ ID NO. 46) |
| BG-Trp-Gly-Pro-Met-PI | (Trp-Gly-Pro-Met = SEQ ID NO. 47) |
| BG-Trp-Gly-Pro-Phe-PI | (Trp-Gly-Pro-Phe = SEQ ID NO. 48) |
| BG-Trp-Gly-Pro-Trp-PI | (Trp-Gly-Pro-Trp = SEQ ID NO. 49) |
| BG-Trp-Gly-Pro-Val-PI | (Trp-Gly-Pro-Val = SEQ ID NO. 50) |
| BG-Trp-Lys-Pro-Ala-PI | (Trp-Lys-Pro-Ala = SEQ ID NO. 51) |
| BG-Trp-Lys-Pro-Leu-PI | (Trp-Lys-Pro-Leu = SEQ ID NO. 52) |
| BG-Trp-Lys-Pro-Nle-PI | (Trp-Lys-Pro-Xaa = SEQ ID NO. 53) |
| BG-Trp-Lys-Pro-Met-PI | (Trp-Lys-Pro-Met = SEQ ID NO. 54) |
| BG-Trp-Lys-Pro-Phe-PI | (Trp-Lys-Pro-Phe = SEQ ID NO. 55) |
| BG-Trp-Lys-Pro-Trp-PI | (Trp-Lys-Pro-Trp = SEQ ID NO. 56) |
| BG-Trp-Lys-Pro-Val-PI | (Trp-Lys-Pro-Val = SEQ ID NO. 57) |
| BG-Phe-Ala-Pro-Ala-PI | (Phe-Ala-Pro-Ala = SEQ ID NO. 58) |
| BG-Phe-Ala-Pro-Leu-PI | (Phe-Ala-Pro-Leu = SEQ ID NO. 59) |
| BG-Phe-Ala-Pro-Nle-PI | (Phe-Ala-Pro-Xaa = SEQ ID NO. 60) |
| BG-Phe-Ala-Pro-Met-PI | (Phe-Ala-Pro-Met = SEQ ID NO. 61) |
| BG-Phe-Ala-Pro-Phe-PI | (Phe-Ala-Pro-Phe = SEQ ID NO. 62) |
| BG-Phe-Ala-Pro-Trp-PI | (Phe-Ala-Pro-Trp = SEQ ID NO. 63) |
| BG-Phe-Ala-Pro-Val-PI | (Phe-Ala-Pro-Val = SEQ ID NO. 64) |
| BG-Phe-Gly-Pro-Ala-PI | (Phe-Gly-Pro-Ala = SEQ ID NO. 65) |
| BG-Phe-Gly-Pro-Leu-PI | (Phe-Gly-Pro-Leu = SEQ ID NO. 66) |
| BG-Phe-Gly-Pro-Nle-PI | (Phe-Gly-Pro-Xaa = SEQ ID NO. 67) |
| BG-Phe-Gly-Pro-Met-PI | (Phe-Gly-Pro-Met = SEQ ID NO. 68) |
| BG-Phe-Gly-Pro-Phe-PI | (Phe-Gly-Pro-Phe = SEQ ID NO. 69) |
| BG-Phe-Gly-Pro-Trp-PI | (Phe-Gly-Pro-Trp = SEQ ID NO. 70) |
| BG-Phe-Gly-Pro-Val-PI | (Phe-Gly-Pro-Val = SEQ ID NO. 71) |
| BG-Phe-Lys-Pro-Ala-PI | (Phe-Lys-Pro-Ala = SEQ ID NO. 72) |
| BG-Phe-Lys-Pro-Leu-PI | (Phe-Lys-Pro-Leu = SEQ ID NO. 73) |
| BG-Phe-Lys-Pro-Nle-PI | (Phe-Lys-Pro-Xaa = SEQ ID NO. 74) |
| BG-Phe-Lys-Pro-Met-PI | (Phe-Lys-Pro-Met = SEQ ID NO. 75) |
| BG-Phe-Lys-Pro-Phe-PI | (Phe-Lys-Pro-Phe = SEQ ID NO. 76) |
| BG-Phe-Lys-Pro-Trp-PI | (Phe-Lys-Pro-Trp = SEQ ID NO. 77) |
| BG-Phe-Lys-Pro-Val-PI | (Phe-Lys-Pro-Val = SEQ ID NO. 78) |
| BG-Ada-Ala-Pro-Ala-PI | (Xaa-Ala-Pro-Ala = SEQ ID NO. 79) |
| BG-Ada-Ala-Pro-Leu-PI | (Xaa-Ala-Pro-Leu = SEQ ID NO. 80) |

| | |
|---|---|
| BG-Ada-Ala-Pro-Nle-PI | (Xaa-Ala-Pro-Xaa = SEQ ID NO. 81) |
| BG-Ada-Ala-Pro-Met-PI | (Xaa-Ala-Pro-Met = SEQ ID NO. 82) |
| BG-Ada-Ala-Pro-Phe-PI | (Xaa-Ala-Pro-Phe = SEQ ID NO. 83) |
| BG-Ada-Ala-Pro-Trp-PI | (Xaa-Ala-Pro-Trp = SEQ ID NO. 84) |
| BG-Ada-Ala-Pro-Val-PI | (Xaa-Ala-Pro-Val = SEQ ID NO. 85) |
| BG-Ada-Gly-Pro-Ala-PI | (Xaa-Gly-Pro-Ala = SEQ ID NO. 86) |
| BG-Ada-Gly-Pro-Leu-PI | (Xaa-Gly-Pro-Leu = SEQ ID NO. 87) |
| BG-Ada-Gly-Pro-Nle-PI | (Xaa-Gly-Pro-Xaa = SEQ ID NO. 88) |
| BG-Ada-Gly-Pro-Met-PI | (Xaa-Gly-Pro-Met = SEQ ID NO. 89) |
| BG-Ada-Gly-Pro-Phe-PI | (Xaa-Gly-Pro-Phe = SEQ ID NO. 90) |
| BG-Ada-Gly-Pro-Trp-PI | (Xaa-Gly-Pro-Trp = SEQ ID NO. 91) |
| BG-Ada-Gly-Pro-Val-PI | (Xaa-Gly-Pro-Val = SEQ ID NO. 92) |
| BG-Ada-Lys-Pro-Ala-PI | (Xaa-Lys-Pro-Ala = SEQ ID NO. 93) |
| BG-Ada-Lys-Pro-Leu-PI | (Xaa-Lys-Pro-Leu = SEQ ID NO. 94) |
| BG-Ada-Lys-Pro-Nle-PI | (Xaa-Lys-Pro-Xaa = SEQ ID NO. 95) |
| BG-Ada-Lys-Pro-Met-PI | (Xaa-Lys-Pro-Met = SEQ ID NO. 96) |
| BG-Ada-Lys-Pro-Phe-PI | (Xaa-Lys-Pro-Phe = SEQ ID NO. 97) |
| BG-Ada-Lys-Pro-Trp-PI | (Xaa-Lys-Pro-Trp = SEQ ID NO. 98) |
| BG-Ada-Lys-Pro-Val-PI | (Xaa-Lys-Pro-Val = SEQ ID NO. 99) |
| BG-Pgl-Ala-Pro-Ala-PI | (Xaa-Ala-Pro-Ala = SEQ ID NO. 100) |
| BG-Pgl-Ala-Pro-Leu-PI | (Xaa-Ala-Pro-Leu = SEQ ID NO. 101) |
| BG-Pgl-Ala-Pro-Nle-PI | (Xaa-Ala-Pro-Xaa = SEQ ID NO. 102) |
| BG-Pgl-Ala-Pro-Met-PI | (Xaa-Ala-Pro-Met = SEQ ID NO. 103) |
| BG-Pgl-Ala-Pro-Phe-PI | (Xaa-Ala-Pro-Phe = SEQ ID NO. 104) |
| BG-Pgl-Ala-Pro-Trp-PI | (Xaa-Ala-Pro-Trp = SEQ ID NO. 105) |
| BG-Pgl-Ala-Pro-Val-PI | (Xaa-Ala-Pro-Val = SEQ ID NO. 106) |
| BG-Pgl-Gly-Pro-Ala-PI | (Xaa-Gly-Pro-Ala = SEQ ID NO. 107) |
| BG-Pgl-Gly-Pro-Leu-PI | (Xaa-Gly-Pro-Leu = SEQ ID NO. 108) |
| BG-Pgl-Gly-Pro-Nle-PI | (Xaa-Gly-Pro-Xaa = SEQ ID NO. 109) |
| BG-Pgl-Gly-Pro-Met-PI | (Xaa-Gly-Pro-Met = SEQ ID NO. 110) |
| BG-Pgl-Gly-Pro-Phe-PI | (Xaa-Gly-Pro-Phe = SEQ ID NO. 111) |
| BG-Pgl-Gly-Pro-Trp-PI | (Xaa-Gly-Pro-Trp = SEQ ID NO. 112) |
| BG-Pgl-Gly-Pro-Val-PI | (Xaa-Gly-Pro-Val = SEQ ID NO. 113) |
| BG-Pgl-Lys-Pro-Ala-PI | (Xaa-Lys-Pro-Ala = SEQ ID NO. 114) |
| BG-Pgl-Lys-Pro-Leu-PI | (Xaa-Lys-Pro-Leu = SEQ ID NO. 115) |
| BG-Pgl-Lys-Pro-Nle-PI | (Xaa-Lys-Pro-Xaa = SEQ ID NO. 116) |
| BG-Pgl-Lys-Pro-Met-PI | (Xaa-Lys-Pro-Met = SEQ ID NO. 117) |
| BG-Pgl-Lys-Pro-Phe-PI | (Xaa-Lys-Pro-Phe = SEQ ID NO. 118) |
| BG-Pgl-Lys-Pro-Trp-PI | (Xaa-Lys-Pro-Trp = SEQ ID NO. 119) |
| BG-Pgl-Lys-Pro-Val-PI | (Xaa-Lys-Pro-Val = SEQ ID NO. 120) |
| BG-Hex-Ala-Pro-Ala-PI | (Xaa-Ala-Pro-Ala = SEQ ID NO. 121) |
| BG-Hex-Ala-Pro-Leu-PI | (Xaa-Ala-Pro-Leu = SEQ ID NO. 122) |
| BG-Hex-Ala-Pro-Nle-PI | (Xaa-Ala-Pro-Xaa = SEQ ID NO. 123) |
| BG-Hex-Ala-Pro-Met-PI | (Xaa-Ala-Pro-Met = SEQ ID NO. 124) |
| BG-Hex-Ala-Pro-Phe-PI | (Xaa-Ala-Pro-Phe = SEQ ID NO. 125) |
| BG-Hex-Ala-Pro-Trp-PI | (Xaa-Ala-Pro-Trp = SEQ ID NO. 126) |
| BG-Hex-Ala-Pro-Val-PI | (Xaa-Ala-Pro-Val = SEQ ID NO. 127) |
| BG-Hex-Gly-Pro-Ala-PI | (Xaa-Gly-Pro-Ala = SEQ ID NO. 128) |
| BG-Hex-Gly-Pro-Leu-PI | (Xaa-Gly-Pro-Leu = SEQ ID NO. 129) |
| BG-Hex-Gly-Pro-Nle-PI | (Xaa-Gly-Pro-Xaa = SEQ ID NO. 130) |
| BG-Hex-Gly-Pro-Met-PI | (Xaa-Gly-Pro-Met = SEQ ID NO. 131) |
| BG-Hex-Gly-Pro-Phe-PI | (Xaa-Gly-Pro-Phe = SEQ ID NO. 132) |
| BG-Hex-Gly-Pro-Trp-PI | (Xaa-Gly-Pro-Trp = SEQ ID NO. 133) |
| BG-Hex-Gly-Pro-Val-PI | (Xaa-Gly-Pro-Val = SEQ ID NO. 134) |
| BG-Hex-Lys-Pro-Ala-PI | (Xaa-Lys-Pro-Ala = SEQ ID NO. 135) |
| BG-Hex-Lys-Pro-Leu-PI | (Xaa-Lys-Pro-Leu = SEQ ID NO. 136) |
| BG-Hex-Lys-Pro-Nle-PI | (Xaa-Lys-Pro-Xaa = SEQ ID NO. 137) |
| BG-Hex-Lys-Pro-Met-PI | (Xaa-Lys-Pro-Met = SEQ ID NO. 138) |
| BG-Hex-Lys-Pro-Phe-PI | (Xaa-Lys-Pro-Phe = SEQ ID NO. 139) |
| BG-Hex-Lys-Pro-Trp-PI | (Xaa-Lys-Pro-Trp = SEQ ID NO. 140) |
| BG-Hex-Lys-Pro-Val-PI | (Xaa-Lys-Pro-Val = SEQ ID NO. 141) |

The compounds of the invention also include the following inhibitors, where PI is a compound other than chloromethyl ketone:

| | |
|---|---|
| BG-Ala-Ala-Pro-Ala-PI | (Ala-Ala-Pro-Ala = SEQ ID NO. 142) |
| BG-Ala-Ala-Pro-Leu-PI | (Ala-Ala-Pro-Leu = SEQ ID NO. 143) |
| BG-Ala-Ala-Pro-Nle-PI | (Ala-Ala-Pro-Xaa = SEQ ID NO. 144) |
| BG-Ala-Ala-Pro-Met-PI | (Ala-Ala-Pro-Met = SEQ ID NO. 145) |
| BG-Ala-Ala-Pro-Phe-PI | (Ala-Ala-Pro-Phe = SEQ ID NO. 146) |
| BG-Ala-Ala-Pro-Val-PI | (Ala-Ala-Pro-Val = SEQ ID NO. 147) |

Preferred inhibitors include:

| | |
|---|---|
| BG-Ala-Ala-Pro-Trp-PI | (includes SEQ ID NO. 1) |
| BG-Ala-Lys-Pro-Phe-PI | (includes SEQ ID NO. 13) |
| BG-Trp-Ala-Pro-Leu-PI | (includes SEQ ID NO. 38) |
| BG-Trp-Ala-Pro-Phe-PI | (includes SEQ ID NO. 41) |
| BG-Phe-Ala-Pro-Leu-PI | (includes SEQ ID NO. 59) |
| BG-Phe-Ala-Pro-Leu-PI | (includes SEQ ID NO. 62) |

BG-Ala-Ala-Pro-Leu-PI, when PI is other than chloromethyl ketone (includes SEQ ID NO. 80)

BG-Ala-Ala-Pro-Phe-PI, when PI is other than chloromethyl ketone (includes SEQ ID NO. 83)

Especially preferred inhibitors include:

BG-Ala-Ala-Pro-Trp-PI, when PI is chloromethyl or fluoromethyl ketone (includes SEQ ID NO. 1)

BG-Ala-Lys-Pro-Phe-PI, when PI is chloromethyl or fluoromethyl ketone (includes SEQ ID NO. 13)

BG-Trp-Ala-Pro-Leu-PI, when PI is chloromethyl or fluoromethyl ketone (includes SEQ ID NO. 38)
BG-Phe-Ala-Pro-Phe-PI, when PI is chloromethyl or fluoromethyl ketone (includes SEQ ID NO. 41)
BG-Phe-Ala-Pro-Leu-PI, when PI is chloromethyl or fluoromethyl ketone (includes SEQ ID NO. 59)
BG-Phe-Ala-Pro-Phe-PI, when PI is chloromethyl or fluoromethyl ketone (includes SEQ ID NO. 62)

The peptide blocking groups which may be attached to $AA_A$ include those well known in the art of peptide synthesis. For example, a listing of suitable peptide blocking groups is found in Gross, et al., eds., *The Peptides*, Vol. 3 (Academic Press, New York, N.Y. 1981). The particular choice of blocking group used in the compounds of the invention depends on several factors, including the blocking group's affect on enzyme specificity, its affect on substrate solubility, and its utility during synthesis. Suitable blocking groups include but are not limited to acetyl; benzoyl; benzyloxy; carbobenzoxy (Cbz), glutaryl, methoxysuccinyl (MeO-Suc), p-tolylsulfonyl (Tos), succinyl, t-butoxycarbonyl (Boc), and certain D-isomers of naturally occuring L-amino acids, including but not limited to D-proline, D-valine, and D-alanine. Preferred blocking groups include benzoyl, benzyloxy, carbobenzoxy, glutaryl, t-butoxycarbonyl, succinyl, methoxysuccinyl, D-Pro, D-Val, D-Ala, and D-Phe.

Enzyme inhibitors that may be attached to $AA_D$ include natural or synthetic compounds that act on the reactive site of a protease to inhibit its activity as an enzyme. (Inhibition is defined herein as the initial binding of the inhibitors to the recognition site of the protease, preferably followed by irreversible covalent bonding of the inhibitor to the active site of the enzyme.) Preferred enzyme inhibitors include, but are not limited to, halo methyl ketones, especially chloromethyl ketones and fluoromethyl ketones. (According to the teaching of the invention, the halo methyl ketones can be mono-halo methyl ketones, di-halo methyl ketones or tri-halo methyl ketones. Also according to the teaching of the invention, mono-chloromethyl ketone and tri-fluoromethyl ketone are preferred protease inhibitors.) In the synthesis of alpha amino chloromethyl ketones, an amino diazomethyl ketone is treated with HCl to synthesize the desired end product. See generally, *Chemistry and Biochemistry of Amino Acids, Peptides and Proteins*, Marcel Dekker, New York, N.Y. 1977; The Peptides, (Gross and Meienhofer, eds.), Academic Press, New York, N.Y. (1981); *Chemistry of Amino Acids*, (Greenstein and Winitz, eds.), Wiley Publications. Synthesis of alpha amino fluoromethyl ketone is disclosed in U.S. Pat. No. 4,518,528 which issued May 21, 1985 to Rasnick. In summary, alpha amino fluoro ketones may be synthesized by suspending a peptide derivative of N-acylamino acid with about two equivalents of fluoroacetic anhydride in an inert solvent. The solvent is added in an amount equal to about the weight of the peptide derivative of the N-acylamino acid. A tertiary amine is then added in an amount of about two equivalents of the peptide derivative of the N-acylamino acid and cooled to a temperature of about 0° C. Thereafter, a catalytic amount of a substituted 4-dialkylaminopyridine catalyst is added and the ketone synthesized.

The invention also includes a method for inhibiting or preventing invasion of skin by schistosome larvae. According to the method, skin is contacted a carrier containing at least one tetrapeptide inhibitor compound comprised of BG-$AA_A$-$AA_B$-$AA_C$-$AA_D$-PI wherein: BG is a peptide blocking group; $AA_A$ is Ala, Gly, Trp, Phe Adamantyl, Phenylglycine, Hexafluoroisoprppyl; $AA_B$ is Ala, Gly or Lys; $AA_C$ is Pro; $AA_D$ is Leu, Nle (Norleucine), Met, Phe, Trp, Val or Ala; and PI is a protease inhibitor, under protease inhibiting conditions in an amount sufficient to inhibit the protease at its reactive site. Protease inhibiting conditions are pH of from about 4–10, preferably from about 6–9, most preferably about 6–8. According to the invention, the carrier can be any suitable lotion, cream, spray, etc. Preferably the carrier will be relatively insoluble in water. Alternatively, the carrier can be soap. According to the teaching of the invention, other compounds that inhibit or prevent invasion of skin by schistosome larvae, e.g., niclosamide, can be used in conjunction with the inhibitory compounds of the present invention. Such compounds could be added to the carrier along with the compounds of the present invention.

The following examples are offered by way of illustration and not by limitation.

EXPERIMENTAL

EXAMPLE 1

Testing of Synthetic Peptide Inhibitors and Substrates Predicted to be Optimal for the Enzyme by the Computer Model The tetrapeptide compounds of the present invention were designed using a computer model of serine protease. This example discusses enzyme inhibitors predicted to be optimal by the computer model.

The P-1 site: The structure of α-lytic protease mutant Met→Ala 192 with a tetrapeptide protease inhibitor has been determined crystallographically (Bone et al., 1987. *Biochemistry* 26, 7609–7614.) The tetrapeptide inhibitor backbone mutant from this x-ray structure was used to position a peptide substrate in the active site of the cercarial protease model.

The validity of the model was first tested by studying the binding specificity of the S-1 cleft of the enzyme. The S-1 cleft in the model is large and hydrophobic, suggesting that a large hydrophobic amino acid at the P-1 position would be bound optimally. This was confirmed by examining a set of synthetic peptide substrates in which both the P-1 amino acid and the leaving group was varied (Table 1). Regardless of the leaving group used to detect substrate hydrolysis, a large hydrophobic amino acid at P-1 always gave the most optimal substrate. The predictions of S-1 binding site specificity were also borne out when examining a set of tetrapeptide inhibitors (Table 2). Phenylalanine and leucine at P-1 gave optimal $k_3/K_i$.

There was a preference for substrates with the smaller thiobenzyl and paranitroaniline leaving groups over the bulkier aminomethylcoumarin derivatives (Table 1). The differences in $k_{cat}/K_m$ noted between the nitroanilide and thioester substrates is probably due to differences in the rate limiting step. The thioesters are much more reactive and the acylation rate is very fast. The rate limiting step is probably deacylation. In contrast, acylation and deacylation rates are similar for the nitroanilide substrates, and in some cases acylation is rate limiting (Stein et al., 1987. *Biochemistry* 26, 1301–1305).

Table 1 shows that the increases noted in $k_{cat}/K_m$ for the best substrates often result more from differences in $k_{cat}$ than $K_m$. This may reflect nonproductive binding of the substrates with respect to the "catalytic register" (Craik et al., 1985. *Science* 228, 291-297). $K_m$ is affected by all possible productive and nonproductive binding domains. But even when the substrate is bound well, position with respect to the catalytic apparatus may not be optimal, resulting in incorrect orientation of the nucleophile relative to the scissile bond (Jencks, 1987. In *Catalysis in Chemistry and Enzymology*. Dover edition, pp 291-296, Dover Publications, Inc., New York).

The size limitations of the P-1 residue were also explored. For substrate hydrolysis, the optimal side chain size appears to be phenylalanine. Leucine at P-1 is the best chloromethyl ketone inhibitor. Tryptophan defines the size limit of the P-1 pocket: the substrate analog MeO-Suc-Ala-Ala-Pro-Trp-Sbzl is a poor substrate, but the chloromethyl ketone inhibitor MeO-Suc-Ala-Ala-Pro-Trp-CMK is still reasonable, with a 20 micromolar inhibition constant. According to the model, tryptophan can fit into the P-1 pocket, but distortion in $x_2$ away from the optimal value is required to ameliorate some steric conflicts. Residue 185 of cercarial protease is leucine. This position is equivalent to residue 189 in the chymotrypsin numbering scheme. Trypsin has an aspartate at this position which gives the enzyme specificity towards positively-charged substrates. Chymotrypsin, which prefers large, hydrophobic residues, has a serine at position 189. The size limitation of the chymotrypsin $S_1$ pocket appears to be slightly larger than cercarial protease (Dorovska et al., 1972. *FEBS Lett.* 23, 122-124). This is sensible given the size difference between leucine and serine.

Beta-branching of the P-1 amino acid significantly reduced activity of both substrates and inhibitors (Table 2). This observation provided an opportunity to use the model as a tool to identify specific residues that might sterically hinder beta-branched amino acids in P-1. In the model structure, beta-branching at P-1 would result in a steric conflict with residue Pro 188. Pro 188 occurs in a loop extension unique to the cercarial protease. Most other eukaryotic serine proteases have Cys at the position analogous to 187 (191 chymotrypsin numbering) that participates in a disulfide bridge. This covalent crosslink, which pulls the loop (residues 189-192) away from the P-1 binding pocket, is replaced by alanine in the cercarial protease. This may result in a constriction of the S-1 pocket.

The P-2 site: Proline in the P-2 site was not altered in the peptide inhibitors of the invention, since it was thought that the restricted geometry enhanced binding. For α-lytic protease, substituting alanine for proline at this position reduces $k_{cat}/K_m$ by a factor of ten (Bone et al., 1987. *Biochemistry* 26, 7609-7614).

The P-3 site: The P-3 site is solvent exposed. A hydrophilic residue at this position should improve solubility, while not affecting binding affinity.

The P-4 site: While P-1 specificity of the cercarial protease was similar to chymotrypsin, an unexpected prediction of the model was that the cercarial enzyme would tolerate bulkier hydrophobic side chains at the P-4 subsite than chymotrypsin. As compared to chymotrypsin, the P-4 site is much more exposed in the cercarial protease—a loop which hangs over this site in chymotrypsin is missing. This loop is situated between residues 159 and 162 in the cercarial protease sequential numbering and contains residues 170 through 178 in the proteases of known three-dimensional structure. Given the lack of this loop, it was speculated that a large side chain on the inhibitor or substrate could fit at the P-4 subsite. To test this prediction, substrates with large, hydrophobic amino acids (Phe, Trp) at this position were assayed. These large amino acids substantially abolished or diminished substrate hydrolysis (Table 1). However, chloromethyl ketone inhibitors with tryptophan at P-4 and phenylalanine or leucine at P-1 worked well (Table 2). It is possible that the interaction of large hydrophobic residues at P-4 with the residues lining the P-4 pocket distorts the geometry of the scissile bond relative to the active site without destroying binding affinity for the inhibitor. The lower $k_3/K_i$ for MeO-Suc-Trp-Ala-Pro-Phe-CMK versus MeO-Suc-Trp-Ala-Pro-Leu-CMK suggests that the conformational flexibility of the leucine side chain is useful in filling the P-1 pocket when the tetrapeptide-CMK has been anchored to the binding cleft by the interaction of tryptophan with the P-4 pocket. This echoes the nonproductive binding of tryptophan to the P-4 pocket in the tetrapeptide substrate analogs.

EXAMPLE II

Assay of Protease with Peptide Substrates

Serine protease was isolated from the acetabular glands of cercariae as described previously in McKerrow et al., 1985. *J. Biol. Chem.* 260, 3703-3707. All tetrapeptide thioester (Sbzl) substrates with the exception of MeO-Suc-Ala-Ala-Pro-Lys-Sbzl (a gift from Dr. James C. Powers, School of Chemistry, Georgia Institute of Technology, Atlanta, Ga.) were purchased from Enzyme System Products (Dublin, Calif.). Stock solutions (25 mM) of all substrates were prepared in dimethyl sulfoxide (DMSO). Rates of hydrolysis of substrates were measured by adding 1-10 μl of substrate and 25 μl of 1 mM 4,4'-dithiodipyridine in DMSO to buffer (100 mM glycine/NaOH, 2 mM $CaCl_2$, pH 9.0) to give a total volume of 1.0 ml. A 10 μl enzyme sample was added to start the reaction. The increase in the absorbance at 325 nm was followed on a Gilford spectrophotometer. An ε value of 19,800 was used for the thiopyridine production.

Assays of paranitroanilide (pNA) and 7-amino-4-methyl coumarin (AMC) derivatized peptides were carried out as described in McKerrow et al., 1985. *J. Biol. Chem.* 260, 3703-3707. MeO-Suc-Ala-Ala-Pro-Phe-pNA was from Vega Biochemicals, Tucson, Az. MeO-Suc-Ala-Ala-Pro-Leu-pNA was a gift of Dr. David Agard, Department of Biochemistry, UCSF. All other pNA substrates were a gift of Dr. Corey Largman, Veterans Administration Hospital, Martinez, Calif. All AMC substrates were from Enzyme Systems Products, Dublin, Calif.

For each peptide substrate, the substrate concentration range was varied over ten-fold. The kinetic constants were determined from the initial rates of product formation using a least squares analysis according to method of Lineweaver-Burk (Lineweaver, H. & Burk, D. 1934. *J. Am. Chem. Soc.* 56, 658). Five points were measured for each plot and correlation co-efficients were all greater than 0.95. See Table 1.

EXAMPLE III

Testing of Synthetic Peptide Inhibitors Versus Purified Protease

This example demonstrates inactivation of serine protease with synthetic protease inhibitors of the invention.

The chloromethyl ketone-derivatized peptide inhibitors were designed by us based on our computer model, and synthesized for us by Enzyme System Products (Dublin, Calif.). Stock solutions of inhibitors (25 mM) were prepared in dimethyl sulfoxide (DMSO). The rate of irreversible inactivation of the protease was followed by withdrawing a 25 μl sample at 4 time intervals after mixing 125 μl of enzyme with 5 μl of inhibitor. Kitz and Wilson's methods of analysis were used for calculation of $K_i$, $k_3$, and $k_3/K_i$ (Kitz R. & Wilson, I. B. 1962. *J. Biol. Chem.* 237, 3245) using MeO-Suc-Ala-Ala-Pro-Phe-Sbzl (Sbzl, benzyl thioester) as substrate. Inactivation constants for the boronic acid-derivatized peptides (MeO-Suc-Ala-Ala-Pro (D or L) boro-Phe-OH, a gift from Dr. Charles Kettner, E. I. Dupont de Nemours, Wilmington, Del.) were calculated using MeO-Suc-Ala-Ala-Pro-Phe-Sbzl as the substrate at 125 and 250 μM. Five different concentrations of each inhibitor were used per substrate concentration. The data were plotted according to Dixon and $k_{inactivation}$ values were extrapolated from the graph (Dixon, 1953. *Biochem. J.* 55, 170–171). See Tables 2 and 3.

EXAMPLE IV

Testing of Inhibitors for their Effect on Cercarial Penetration of Human Skin

A modification of the assay developed by Clegg and Smithers (Clegg & Smithers, 1972. *Int. J. Parasitol.* 2, 79–98.) was used. Two Plexiglass chambers were manufactured which could be screwed together to hold a 25×25 mm section of skin at the interface of the two chambers. Human skin was obtained from autopsy (6–12 hours following death) or from amputation specimens received at the Department of Surgical Pathology, UCSF. The chamber below the skin was filled with tissue culture medium (DME H16) prewarmed to 37° C. After the skin was clamped, the upper chamber was filled with water containing 9000 cercariae of *Schistosoma mansoni* (Puerto Rican strain). Cercariae will follow a thermal gradient, and they are stimulated by the lipid on the surface of skin to invade (Stirewalt, 1974. *Adv. Parasitol.* 12, 115–180). After one hour exposure to cercariae the skin was removed, fixed in 10% phosphate buffered formalin for 24 h, and sectioned at 2 mm intervals. Following dehydration and routine paraffin embedding, 5μ sections were cut by microtome and stained with hemotoxylin and eosin. The number of cercariae which had invaded epidermis or dermis was counted in each section. Percent inhibition of invasion was calculated as $$\left(1.0 - \frac{\text{Number of cercariae invaded with inhibitor}}{\text{Number of cercariae invaded by control}}\right) \times 100\%$$

All assays were done in triplicate and standard deviation of the mean calculated.

EXAMPLE V Effect of Peptide Inhibitors on Cercarial Penetration of Human Skin Based on the observations from structural modeling of the cercarial protease, and the subsequent data from assays of synthetic peptide substrates and inhibitors, a series of chloromethyl ketone and boronic acid derivatized tetrapeptides were tested against live cercariae in an in vitro model of human skin penetration. When cercariae were introduced into a chamber containing human skin warmed to 37° C., they were attracted to the skin surface and stimulated to invade by lipid on the surface of skin. Within one hour cercariae could be observed entering the dermal extracellular matrix. In the concentration range of peptide inhibitors tested (20 μM to 1 mM), boronic acid derivatized peptides and chloromethyl ketone derivatized peptides had no effect on cercarial motility, movement toward skin, or viability. In fact, even if inhibited from invading, cercariae still swim to and attach to the surface of skin by mucous secretions in the presence of these inhibitors.

Tetrapeptide inhibitors with large hydrophobic P-1 side chains (Leu, Phe), predicted by the model to be favored by the enzyme, were effective in inhibiting cercarial penetration of skin at 50 μM. In contrast, a chloromethyl ketone-derivatized tetrapeptide, differing only in having a small hydrophobic amino acid at P-1 (Ala) had no significant effect on cercarial invasion.

The solubility of these hydrophobic chloromethyl ketone peptides is limited at 50 μM. Therefore the possibility of using the model to design an inhibitor with increased solubility was examined. The P-3 side chain of the modeled inhibitor points away from the protein in the direction of the solvent, suggesting that any amino acid could be sterically accommodated at this position. A hydrophilic amino acid should increase inhibitor solubility. Table 2 shows that a synthetic peptide with lysine at P-3 was only slightly less effective at inhibiting the protease ($k_3/K_i$ of 563 $M^{-1}$ $sec^{-1}$ versus 798 $M^{-1}$ $sec^{-1}$ for the "parent" peptide) but its aqueous solubility increased from 50 μM to 200 μM. At this higher concentration, 85% of the cercariae were inhibited from invading skin.

Boronic acid derivatized peptides have greater solubility relative to the corresponding chloromethyl ketone peptides. Therefore a boronic acid derivatized peptide analogous to the chloromethyl ketone derivatized Ala-Ala-Pro-Phe sequence was also tested. The inhibitory capacity (measured as $IC_{50}$ because the chloromethyl ketone inhibitor is irreversible while the boronic acid inhibitor is not) of the two peptides against purified enzyme was similar (Table 3). The more soluble boronic acid inhibitor was then used to confirm inhibition of skin penetration at varying concentrations of inhibitor. Stereoisomers of the same peptide were also evaluated. At 50 micromolar the L-stereoisomer inhibited 50% of cercariae from invading skin while the D-stereoisomer inhibited less than 20%. This was consistent with the preference of the protease for L amino acids (Table 2).

TABLE 1

Kinetic Constants for the Hydrolysis of Tetrapeptide Substrates by the Cercarial Protease[a]

| Substrate P-4 P-3 P-2 P-1 | $K_m$ μM | $k_{cat}$ $s^{-1}$ | $k_{cat}/K_m$ $M^{-1}s^{-1}$ |
|---|---|---|---|
| MeO-Suc-Ala-Ala-Pro-Phe-Sbzl | 96 | 19.4 | 202,100 |
| MeO-Suc-Ala-Ala-Pro-Leu-Sbzl | 464 | 7.5 | 16,200 |
| MeO-Suc-Ala-Ala-Pro-Val-Sbzl | very low activity[b] | | |
| MeO-Suc-Ala-Ala-Pro-Ala-Sbzl | no activity | | |
| MeO-Suc-Ala-Ala-Pro-Lys-Sbzl | no activity | | |
| MeO-Suc-Phe-Ala-Pro-Phe-Sbzl | 244 | 3.48 | 14,000 |
| MeO-Suc-Trp-Ala-Pro-Phe-Sbzl | no activity | | |
| MeO-Suc-Ala-Ala-Pro-Leu-pNA | 118 | 0.33 | 2800 |
| MeO-Suc-Ala-Ala-Pro-Phe-pNA | 119 | 0.19 | 1600 |
| MeO-Suc-Ala-Ala-Pro-Met-pNA | 300 | 0.05 | 185 |
| MeO-Suc-Ala-Ala-Pro-Nle-pNA | 300 | 0.02 | 56 |
| MeO-Suc-Ala-Ala-Pro-Val-pNA | very low activity[b] | | |
| MeO-Suc-Ala-Ala-Pro-Ile-pNA | very low activity[b] | | |
| MeO-Suc-Ala-Ala-Pro-Phe-AMC | low but detectable activity | | |
| MeO-Suc-Ala-Ala-Pro-Val-AMC | no activity | | |

TABLE 1-continued

Kinetic Constants for the Hydrolysis of Tetrapeptide Substrates by the Cercarial Protease[a]

| Substrate<br>P-4 P-3 P-2 P-1 | $K_m$<br>$\mu M$ | $k_{cat}$<br>$s^{-1}$ | $k_{cat}/K_m$<br>$M^{-1}s^{-1}$ |
|---|---|---|---|
| MeO-Suc-Ala-Ala-Pro-Ala-AMC | | no activity | |

[a] $r^2$ for plots were 0.95->0.99. P-1, P-2, etc. refer to the position of residues relative to the site of enzyme catalyzed cleavage (I. Schecter). In this case the bond between the peptide and the Sbzl (benzyl thioester), pNA (paranitroanilide) or AMC (7-amino-4-methyl coumarin) leaving groups (which allow spectrophotometric or spectrofluorometric measurement) is the one cleaved. The S-1 binding pocket of the enzyme woudl accomodate the P-1 side chain. MeO-Suc = methoxysuccinyl blocking group.
[b] Absorbance change less than 0.001 O.D. in 40 min with 1.5 mM substrate.

TABLE 2

Inhibition of Cercarial Protease by Chloromethyl Ketone Derivatized Peptides[a]

| Inhibitors<br>P-4 P-3 P-2 P-1 | $K_i$<br>$(\mu M)$ | $k_3$<br>$(sec^{-1} \times 10^3)$ | $k_3K_i$<br>$(M^{-1} sec^{-1})$ |
|---|---|---|---|
| MeO-Suc-Ala-Ala-Pro-Leu-CMK | 12 | 18 | 1485 |
| MeO-Suc-Ala-Ala-Pro-Phe-CMK | 13 | 11 | 798 |
| MeO-Suc-Ala-Ala-Pro-Trp-CMK | 20 | 10 | 493 |
| MeO-Suc-Ala-Ala-Pro-Val-CMK | No inhibition | | 13[b] |
| MeO-Suc-Ala-Ala-Pro-Ala-CMK | No inhibition | | 0.7[b] |
| MeO-Suc-Ala-Lys-Pro-Phe-CMK | 7 | 37 | 563 |
| MeO-Suc-Ala-Ala-Pro-Leu-CMK | 12 | 18 | 1485 |
| MeO-Suc-Trp-Ala-Pro-Leu-CMK | 2 | 8 | 3846 |
| MeO-Suc-Ala-Ala-Pro-Phe-CMK | 13 | 11 | 798 |
| MeO-Suc-Phe-Ala-Pro-Phe-CMK | 1 | 6 | 5483 |
| MeO-Suc-Trp-Ala-Pro-Phe-CMK | 12 | 6 | 521 |

[a] In Table 2, CMK = chloromethyl ketone. MeO-Suc = methoxysuccinyl blocking group.
[b] These values are $k_{observed}/[I]$ which are equal to $k_3K_i$ since $[I] << K_i$.

TABLE 3

Comparison of Chloromethyl Ketone Inhibitors to Boronic Acid Inhibitors versus Cercarial Proteinase

| Inhibitor | $IC_{50}$ at 20 min (nM) |
|---|---|
| MeO-Suc-Ala-Ala-Pro-Leu-CMK | 36 |
| MeO-Suc-Ala-Ala-Pro-Phe-CMK | 88 |
| MeO-Suc-Ala-Ala-Pro-(L)boro-Phe-OH | 136 |
| MeO-Suc-Ala-Ala-Pro-(D)boro-Phe-OH | $>10^4$ |
| MeO-Suc-Ala-Ala-Pro-Ala-CMK | $>10^5$ |

SUMMARY

All publications and patents mentioned in this specification are indicative of the level of skill of those skilled in the art to which this invention pertains. All publications and patents are herein incorporated by reference to the same extent as if each individual publication or patents was specifically and individually indicated to be incorporated by reference.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated.

We claim:

1. A composition of matter comprising $BG\text{-}AA_A\text{-}AA_B\text{-}AA_C\text{-}AA_D\text{-}PI$ wherein:
   BG is a peptide blocking group;

$AA_A\text{-}AA_B\text{-}AA_C\text{-}AA_D$ is selected from the group consisting of Phe-Ala-Pro-Leu and Phe-Ala-Pro-Phe; and PI is a protease inhibitor selected from the group consisting of halo methyl ketones and boronic acid.

2. A composition of matter according to claim 1 wherein BG is a blocking group selected from the group consisting of acetyl, benzoyl, benzyloxy, carbobenzoxy (Cbz), glutaryl, methoxysuccinyl (MeO-Suc), p-tolylsulfonyl (Tos), succinyl, t-butoxycarbonyl (Boc), D-proline, D-valine, D-Leucine, D-Phenylalanine and D-alanine.

3. A composition of matter according to claim 1 wherein said halo methyl ketone is selected from the group consisting of chloromethyl ketone and fluoromethyl ketone.

4. A composition of matter according to claim 3 wherein said chloromethyl ketone is mono-chloromethyl ketone and said fluoromethyl ketone is tri-fluoromethyl ketone.

5. A composition of matter comprising BG-Phe-Ala-Pro-Phe-PI (includes SEQ ID NO. 62) wherein PI is chloromethyl ketone or fluoromethyl ketone.

6. A composition of matter according to claim 5 wherein said chloromethyl ketone is mono-chloromethyl ketone and said fluoromethyl ketone is tri-fluoromethyl ketone.

7. A composition of matter suitable for topical application to skin comprising a suitable carrier and at least one of the compounds selected from the group consisting of BG-Phe-Ala-Pro-Leu-PI and BG-Phe-Ala-Pro-Phe-PI wherein BG is a peptide blocking group and PI is a protease inhibitor selected from the group consisting of halo methyl ketones and boronic acid.

8. A composition according to claim 7 wherein said suitable carrier is a lotion, a cream or a spray.

9. A composition of matter according to claim 7 wherein PI is chloromethyl ketone or fluoromethyl ketone.

10. A composition of matter according to claim 9 wherein said chloromethyl ketone is mono-chloromethyl ketone and said fluoromethyl ketone is tri-fluoromethyl ketone.

11. Soap containing at least one of the compounds selected from the group consisting of BG-Phe-Ala-Pro-Leu-PI and BG-Phe-Ala-Pro-Phe-PI.

12. Soap according to claim 11 wherein PI is chloromethyl ketone or fluoromethyl ketone.

13. Soap according to claim 12 wherein said chloromethyl ketone is mono-chloromethyl ketone and said fluoromethyl ketone is tri-fluoromethyl ketone.

14. A method for inhibiting penetration of skin by schistosome larvae, said method comprising contacting skin with a carrier containing an effective an amount of at least one tetrapeptide inhibitor compound selected from the group consisting of BG-Phe-Ala-Pro-Leu-PI and BG-Phe-Ala-Pro-Phe-PI.

15. A method according to claim 14 wherein PI is chloromethyl ketone or fluoromethyl ketone.

16. A method according to claim 15 wherein said chloromethyl ketone is mono-chloromethyl ketone and said fluoromethyl ketone is tri-fluoromethyl ketone.

* * * * *

UNITED STATES PATENT AND TRADEMARK OFFICE
CERTIFICATE OF CORRECTION

PATENT NO. : 5,284,829
DATED : February 8, 1994
INVENTOR(S) : McKerrow et al.

It is certified that error appears in the above-identified patent and that said Letters Patent is hereby corrected as shown below:

Col. 1, line 46, delete "debilatiting" and insert --debilitating--.

Col. 6, line 58, delete "BG-Trp -ALA-PRO-PHE-PI" and insert --BG-Phe-Ala-Pro-Leu-PI--.

Col. 11, line 59, "Example V" should be centered.

Col. 13, line 11, delete "woudl" and insert --would--.

Signed and Sealed this

Thirtieth Day of August, 1994

*Attest:*

BRUCE LEHMAN

*Attesting Officer*     *Commissioner of Patents and Trademarks*